US009474580B2

(12) United States Patent
Hannaford et al.

(10) Patent No.: US 9,474,580 B2
(45) Date of Patent: Oct. 25, 2016

(54) SURGICAL COCKPIT COMPRISING MULTISENSORY AND MULTIMODAL INTERFACES FOR ROBOTIC SURGERY AND METHODS RELATED THERETO

(71) Applicant: SPI Surgical, Inc., Seattle, WA (US)

(72) Inventors: Blake Hannaford, Seattle, WA (US); Louis Kim, Seattle, WA (US); Thomas S. Lendvay, Seattle, WA (US); Kristen S. Moe, Seattle, WA (US); James S. Pridgeon, Seattle, WA (US); Jacob Rosen, Santa Cruz, CA (US); Laligam Sekhar, Seattle, WA (US)

(73) Assignee: SPI SURGICAL, INC., Seattle, WA (US)

( * ) Notice: Subject to any disclaimer, the term of this patent is extended or adjusted under 35 U.S.C. 154(b) by 36 days.

(21) Appl. No.: 14/181,388

(22) Filed: Feb. 14, 2014

(65) Prior Publication Data
US 2015/0025547 A1     Jan. 22, 2015

Related U.S. Application Data

(63) Continuation of application No. 13/051,921, filed on Mar. 18, 2011, now abandoned.

(60) Provisional application No. 61/315,018, filed on Mar. 18, 2010.

(51) Int. Cl.
*A61B 19/00* (2006.01)
*B25J 13/02* (2006.01)
(Continued)

(52) U.S. Cl.
CPC ..... *A61B 19/2203* (2013.01); *A61B 17/00234* (2013.01); *A61B 34/30* (2016.02);
(Continued)

(58) Field of Classification Search
CPC ............ A61B 19/2203; A61B 2017/00973; A61B 17/00234; A61B 34/30; A61B 34/35; A61B 34/74; A61B 34/76; A61B 34/60; B25J 13/02; G06F 3/011; G06F 3/014; G06F 3/016; A61M 29/00
See application file for complete search history.

(56) References Cited

U.S. PATENT DOCUMENTS

| 5,163,949 A | 11/1992 | Bonutti |
| 5,373,854 A | 12/1994 | Kolozsi |

(Continued)

FOREIGN PATENT DOCUMENTS

JP     2002078772 A     3/2002

OTHER PUBLICATIONS

Cyber Force: Cyber Glove Systems Website. Accessed Nov. 19, 2015. http://www.cyberglovesystems.com/cyberforce.
(Continued)

*Primary Examiner* — Richard Louis
(74) *Attorney, Agent, or Firm* — Wilson Sonsini Goodrich & Rosati

(57) ABSTRACT

Local surgical cockpits comprising local surgical consoles that can communicate with any desired remote surgical module (surgical robot), for example via a shared Transmission Control Protocol/Internet Protocol (TCP/IP) or other unified open source communication protocol or other suitable communication system. The systems and methods, etc., herein can also comprise a modular approach wherein multiple surgical consoles can network supporting collaborative surgery regardless of the physical location of the surgeons relative to each other and/or relative to the surgical site. Thus, for example, an operator operating a local surgical cockpit can teleoperate using a remote surgical module on a patient in the same room as the surgeon, or surgeons located in multiple safe locations can telemanipulate remote multiple surgical robots on a patient in or close to a war zone.

20 Claims, 9 Drawing Sheets

(51) Int. Cl.
*G06F 3/01* (2006.01)
*A61M 29/00* (2006.01)
*A61B 17/00* (2006.01)

(52) U.S. Cl.
CPC .............. *A61B 34/35* (2016.02); *A61B 34/74* (2016.02); *A61B 34/76* (2016.02); *A61B 90/60* (2016.02); *A61M 29/00* (2013.01); *B25J 13/02* (2013.01); *G06F 3/011* (2013.01); *G06F 3/014* (2013.01); *G06F 3/016* (2013.01); *A61B 2017/00973* (2013.01)

(56) References Cited

U.S. PATENT DOCUMENTS

| | | | |
|---|---|---|---|
| 5,514,153 A | 5/1996 | Bonutti | |
| 5,776,126 A * | 7/1998 | Wilk et al. | 606/1 |
| 6,179,776 B1 | 1/2001 | Adams et al. | |
| 6,203,559 B1 | 3/2001 | Davis et al. | |
| 6,352,503 B1 | 3/2002 | Matsui et al. | |
| 6,451,042 B1 | 9/2002 | Bonutti | |
| 2002/0128633 A1 | 9/2002 | Brock et al. | |
| 2003/0013949 A1 | 1/2003 | Moll et al. | |
| 2005/0001838 A1 | 1/2005 | Gregorio et al. | |
| 2005/0085691 A1 | 4/2005 | Nakao | |
| 2005/0137460 A1 | 6/2005 | Bertolero et al. | |
| 2005/0206583 A1 | 9/2005 | Lemelson et al. | |
| 2006/0052684 A1 * | 3/2006 | Takahashi et al. | 600/407 |
| 2006/0142657 A1 * | 6/2006 | Quaid et al. | 600/424 |
| 2007/0252821 A1 * | 11/2007 | Hollemans et al. | 345/173 |
| 2008/0058590 A1 | 3/2008 | Saadat et al. | |
| 2008/0167662 A1 * | 7/2008 | Kurtz | 606/130 |
| 2009/0000626 A1 | 1/2009 | Quaid et al. | |
| 2009/0085878 A1 | 4/2009 | Heubel et al. | |
| 2009/0245600 A1 | 10/2009 | Hoffman et al. | |
| 2010/0073150 A1 * | 3/2010 | Olson et al. | 340/407.1 |
| 2011/0046659 A1 * | 2/2011 | Ramstein et al. | 606/205 |
| 2011/0238079 A1 | 9/2011 | Hannaford et al. | |

OTHER PUBLICATIONS

Omega 7 Brochure: Force Dimension website. Accessed Nov. 19, 2015. http://www.forcedimension.com/products/omega-7/overview.

International Search Report and Written Opinion of PCT/US2011/029067 dated Dec. 12, 2011.

International Search Report and Written Opinion of PCT/US2011/029071 dated Nov. 23, 2011.

Office action dated Aug. 15, 2013 for U.S. Appl. No. 13/051,921.

* cited by examiner

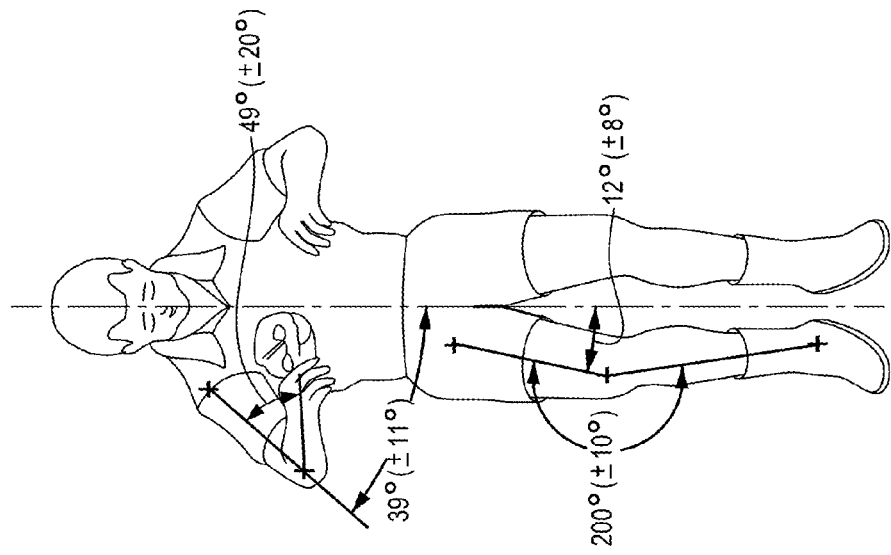
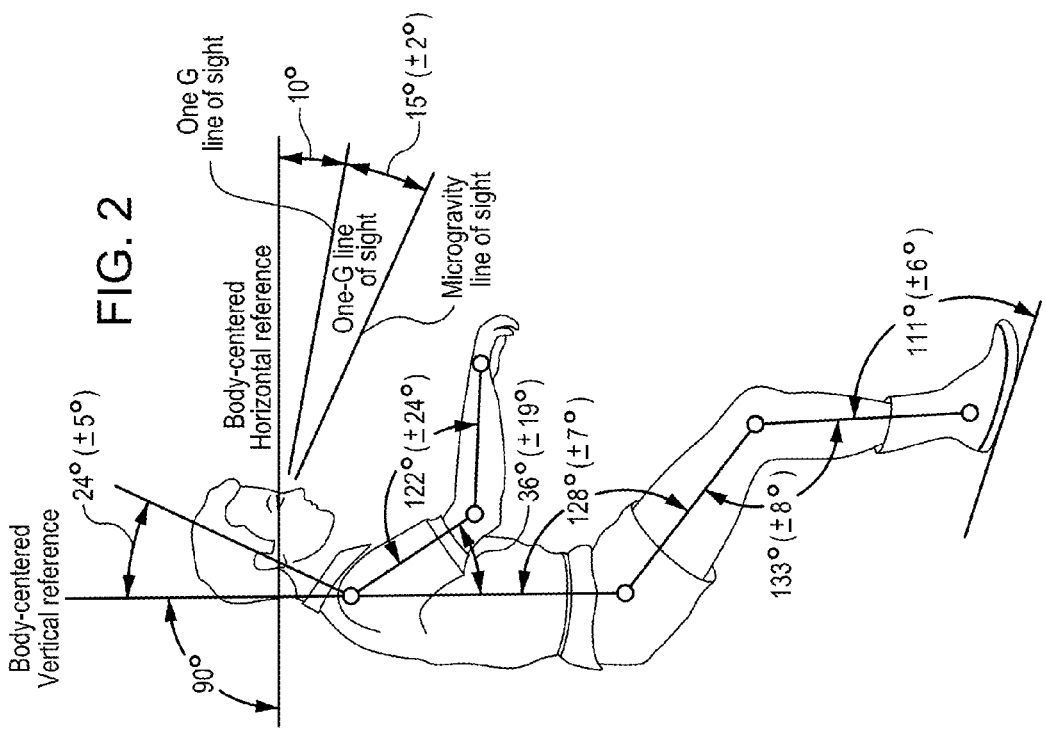

SURGICAL COCKPIT COMPRISING MULTISENSORY AND MULTIMODAL INTERFACES FOR ROBOTIC SURGERY AND METHODS RELATED THERETO

PRIORITY CLAIM

The present application is a continuation of U.S. patent application No. 13/051,921, filed Mar. 18, 2011, which claims the benefit of U.S. Provisional application Ser. No. 61/315,018, filed Mar. 18, 2010, which application is incorporated herein by reference in its entirety.

BACKGROUND OF THE INVENTION

Despite advances in personnel, technology, and force protection, war fighters remain vulnerable to blast wounds, burns, and multiple penetrating injuries not usually encountered in civilian settings. There is a fundamental need to deploy skilled personnel equipped with advanced technology to provide medical and surgical attention as close as possible to the point of injury for a soldier in the battlefield and civilians in a remote location or during natural or manmade disasters. Although war surgery is aimed to treat combat casualties at far forward locations and under austere conditions continues to save lives, the nature of battlefield injuries shortens the "golden hour" in which highly skilled medical attention is required to stabilize the soldier.

One of the major problems in the military and its integrated health services support system to triage, treat, evacuate, and return soldiers to duty is the occasional mismatch between the type of injury and the type of surgeon available to treat it. For example, a heart surgeon may be required to perform a craniotomy. Telemedicine in general and telerobotic surgery in particular are a means to mediate the narrow spectrum of available front line surgical expertise.

There has gone unmet a need for improved methods that provide one or more of the needs indicated above, for example robust telerobotic capabilities so an expert surgeon could perform critical steps of an operation from the continental U.S. or other desired location while the soldier or other patient is located anywhere around the globe.

The present systems and methods, etc., provide these and/or other advantages. Present systems and methods, etc., extend the spectrum of surgical expertise to a level appropriate for the type and nature of battlefield wounds. The present systems and methods, etc., also extend to any desired area of surgery including those well beyond the military arena.

SUMMARY

The present systems and methods, etc., comprise local surgical cockpits comprising local surgical consoles that can communicate with any desired remote surgical module (surgical robot), for example via a shared Transmission Control Protocol/Internet Protocol (TCP/IP) or other unified open source communication protocol or other suitable communication system. The systems and methods, etc., herein can also comprise a modular approach wherein multiple surgical consoles can network supporting collaborative surgery regardless of the physical location of the surgeons or other operators relative to each other and/or relative to the surgical site. Thus, for example, a surgeon operating a local surgical cockpit can teleoperate using a remote surgical module on a patient in the same room as the surgeon, or surgeons located in multiple safe locations can telemanipulate remote multiple surgical robots on a patient in or close to a war zone or any remote location.

One aspect of the systems, methods, etc., herein is to provide a multisensory, multi-modal surgical workstation (surgical cockpit). This workstation can provide a command post allowing the surgeon(s) to visually immerse themselves into the remote surgical space. It provides peripheral information such as vital signs, as well as visual feeds from the operating room (OR) surrounding the actual surgical site on or in the patient. In this way, the surgical console provides high situational awareness as well as the capability to dynamically interact with the other functions of the OR. This is accomplished by multiple streams of visual, audio, and kinesthetic inputs. Special attention can also paid to avoiding information overload of the surgeon.

In a further aspect, the present methods, devices, systems, etc., are related to a local surgical cockpit comprising a base, a frame disposed on the base, a seat for an operator disposed on the frame, and a remote surgical console configured such that the operator can operate the console for remote surgery while in the seat, wherein the seat can be ergonomic and can be operably connected to the frame such that the seat can be retainably tilted from a substantially upright position to a substantially supine position.

In certain embodiments, the seat can comprise an independently moveable headrest, backrest, seating plate and footrest, the seat further comprising positioning elements operably connected to the independently moveable headrest, backrest, seating plate and footrest and providing at least three axes of retainable positioning movement for each of the independently moveable headrest, backrest, seating plate and footrest. The seat can comprise a lumbar support comprising retainable positioning movement for support of the lower back. The reference body posture of the seat can correspond to a human body posture that can be fully relaxed in micro gravity.

The cockpit further can comprise at least one peripheral device operably connected to move with the seat when the seat is moved so that the location of the peripheral device relative to the operator in the seat is substantially unchanged. The peripheral device can be at least one of a monitor facing an operator in the seat and operably linked to display a remote surgical site, a heads-up display disposed in front of the local surgeon's eyes, and an input device disposed at a hand of the operator and operably linked to provide input to a corresponding device located at the remote surgical site.

Another aspect comprises a local surgical cockpit comprising a local surgical console configured for transmitting surgical movements of local surgeon operating the local surgical console to a remote surgery site, and a head-mounted display disposed in front of the local surgeon's eyes in surgical position in the cockpit to operate the console for surgery, wherein the head-mounted display can be configured to depict at least images of a remote surgical site under remote operation by the operator. The local surgical cockpit can be part of a system and the system further can comprise remote image sensors operably connected to the head-mounted display to transmit the image of the remote surgical site. The head-mounted display can extend to the local surgeon's eyes from an articulated boom or other retention structure disposed in front of the local surgeon's eyes, which retention structure can be actuated by at least one hand control located on the cockpit, or by voice control or otherwise as desired. The head-mounted display can be disposed on a head-mounted frame configured to rest on an operator's head and to maintain the images in front of the local surgeon's eyes when the operator's head moves. The head-mounted display can comprise two separate streams of video displayed to each eye of the local surgeon's eyes, each stream comprising corresponding right and left eye views of a remote surgical site to provide a 3-D image of the site.

The cockpit further can comprise at least one monitor operably held to the base of the cockpit, and the head-mounted display can comprise two separate streams of video displayed to each eye of the local surgeon's eyes, each stream comprising corresponding right and left eye views of a remote surgical site to provide a 3-D image of the site. The monitor(s) can also be 3-D.

In another aspect, the systems, etc., are directed to a local surgical cockpit comprising a local surgical console configured for transmitting surgical movements of an operator operating the local surgical console to a remote surgery site, and comprising at least one image display device configured to depict at least one image of the remote surgical site, the display device further depicting augmented reality for the operator comprising augmented information shown on the display and superimposed over the image of the remote surgical site.

The local surgical cockpit can be part of a system and the system further can comprise remote image sensors operably connected to the head-mounted display to transmit the image of the remote surgical site. The augmented information can comprise at least one of preselected margins to dissect during the surgery and a mask of vital structures in the remote surgical site overlaid over the images of the remote surgical site. The display device can further display further augmented information either to a side of or superimposed over the image of the remote surgical site and the further augmented information can comprise at least one of blood pressure, temperature, $O_2$ level, $CO_2$ level, intracranial pressure, a preplanned trajectory for a surgical tool, tool type, suction on/off, a bottom task bar, recording capabilities, current time, and elapsed time. The image of the remote surgical site and the augmented information can comprise blending graphical images with real-world views of the remote surgical sit, and can be provided by at least one of an endoscopic camera, a remote surgical site camera, or a camera showing an operating room.

In still another aspect, the systems, etc., are directed to a local surgical cockpit comprising a local surgical console configured for transmitting surgical movements of an operator operating the local surgical console to a remote surgery site, and comprising a local surgical instrument comprising local input surgical fingers configured to provide input to corresponding remote surgical fingers configured to manipulate a remote surgical instrument at a remote operation site, wherein the local fingers can be high frequency haptic fingers configured to provide tactile feedback to the operator based on acceleration of the remote surgical instrument manipulated by the remote surgical fingers.

The local surgical cockpit can be part of a system and the system further can comprise the remote surgical fingers, and wherein the remote surgical fingers can be haptic fingers configured to provide tactile feedback to the operator based on acceleration of the remote surgical instrument manipulated by the remote surgical fingers.

The local surgical cockpits can be configured such that operators in different locales can operate simultaneously on a single surgical site; such that operators can relieve each other in a single surgery at a single surgical site; or to provide a teaching surgical cockpit and a student surgical cockpit providing haptic feedback to a student operator generated by a teaching operator. The haptic feedback to the student can comprise movements of a remote surgical instrument controlled by the teaching operator or tactile feedback from a surgical site being operated on by the teaching operator.

In a further aspect, the systems, etc., are directed to a local surgical cockpit comprising a local surgical console configured for transmitting surgical movements of an operator operating the local surgical console to a remote surgery site, and comprising at least seven degrees of freedom for a local surgical instrument manipulated by a robotic arm manipulated by the operator, wherein the console can be configured such that the seven degrees of freedom can be transmissible to a remote surgical instrument located at a remote surgical site and manipulated by the operator operating the console.

The local surgical cockpit can be part of a system and the system further can comprise the remote surgical instrument operably connected to the local surgical instrument such that the remote surgical instrument precisely responds in at least seven corresponding degrees of freedom to movements of the local surgical instrument. The degrees of freedom can comprise at least nine degrees of freedom for the local surgical instrument manipulated by the operator and a corresponding nine degrees of freedom for the remote surgical instrument. The degrees of freedom can comprise at least twelve degrees of freedom for the local surgical instrument manipulated by the operator and a corresponding twelve degrees of freedom for the remote surgical instrument, wherein the local robotic arm can comprise a shoulder joint, an elbow joint, a wrist joint and the three fingers, each comprising at least the following degrees of freedom: shoulder can comprise 2 degrees of freedom; elbow can comprise 1 degree of freedom; wrist can comprise 3 degrees of freedom; the three fingers can comprise 2 degrees of freedom each.

The local surgical instrument can comprise at least three input fingers configured to provide input to a corresponding at least three remote surgical fingers configured to manipulate a remote surgical instrument at a remote operation site, wherein the at least three input fingers can be configured to be manipulated by a single hand of an operator operating the local surgical instrument, and wherein the at least seven degrees of freedom can comprise at least two degrees of freedom for two of the three remote surgical fingers and at least three degrees of freedom for a third of the three remote surgical fingers, or the degrees of freedom can comprise at least nine degrees of freedom comprising at least three degrees of freedom for each of the three remote surgical fingers.

The local robotic arm can comprise a shoulder joint, an elbow joint, a wrist joint and the three fingers, each comprising at least the following degrees of freedom: shoulder can comprise 2 degrees of freedom; elbow can comprise 1 degree of freedom; wrist can comprise 3 degrees of freedom; the three fingers can comprise 2 degrees of freedom each. Or he three fingers can comprise 3 degrees of freedom each.

The degrees of freedom provide for variable desired positioning and orientation of a tip of the remote surgical instrument in space in 6 parameters including Cartesian position (x,y,z), and angular orientation (x y z $\theta$, $\theta$, $\theta$). Control of the remote surgical instrument further can comprise scaling factors configured such that motion input by the operator can be attenuated or amplified with respect to the remote surgical instrument. Control further can comprise indexing configured to allow the operator to disengage the input device from the remote surgical instrument to reposition his/her arms and engage again.

In still yet another aspect, the systems, etc., are directed to a local surgical cockpit comprising a local surgical console configured for transmitting surgical movements of an operator operating the local surgical console to a remote surgery site, and comprising a local surgical instrument comprising at least three input fingers configured to provide input to a corresponding at least three remote surgical fingers configured to manipulate a remote surgical instrument at a remote operation site, The at least three input fingers can be configured to be manipulated by a single hand of an operator operating the local surgical instrument.

The local surgical cockpit can be part of a system and the system further can comprise the three remote surgical fingers operably connected to the three input fingers such that the three remote surgical fingers precisely respond to movements of the three input fingers.

The at least three input fingers can be configured to correspond respectively to a) an operator's thumb, b) an operator's index and middle fingers, and c) an operator's ring and little fingers; or to a) an operator's thumb, b) an operator's index finger, and c) an operator's middle, ring and little fingers. The at least three input fingers can be haptic fingers configured to provide tactile feedback to the operator based on acceleration of a remote surgical instrument manipulated by the remote surgical fingers. The three input fingers can be operably connected so that two fingers control remote surgical fingers and the remaining third finger controls an external device, which can be a one or more of an electrocautery device, a laser photocoagulator, a staple applier or other device as desired. The external device can also be an optical aspect of the camera system such as focus, zoom, rotation, or field-of-view.

In another aspect, the systems, etc., are directed to a local surgical cockpit comprising a local surgical console configured for transmitting surgical movements of an operator operating the local surgical console to a remote surgery site, and comprising at least one haptic foot pedal configured to be operably connected to at least one remote device at a remote operation site, wherein the at least one haptic foot pedal can be configured to be manipulated by a foot of the operator operating the local surgical console to cause a movement or control change in the remote device.

The local surgical cockpit can be part of a system and the system further can comprise the at least one remote device operably connected to the at least one haptic foot pedal. The local surgical cockpit further can comprise at least two haptic foot pedals configured to be operably connected to the at least one remote device at the remote operation site. The local surgical cockpit further can comprise at least eight haptic foot pedals configured to be operably connected to at least two remote devices at the remote operation site, the at least eight haptic foot pedals divided to provide at least a first foot pedal set and second foot pedal set, wherein a first foot pedal set and second foot pedal set can be each disposed to be manipulated by a right foot of the operator and by a left foot of the operator, respectively.

If desired, for each of the first foot pedal set and second foot pedal set, the sets can each contain four pedals with each of the four pedals in one of four quadrants of a circle. The pedals can also be set in an array. Opposed or otherwise set off pairs of pedals can be assigned opposed functions at the remote surgical site. The opposed functions can be suction and irrigation. The four pedals can also be assigned complementary functions for a remote instrument at the remote surgical site. The four pedals can control the viewing angles of an endoscopic camera. The local surgical cockpit further can comprise a dead zone that prevents two opposing functions being implemented simultaneously.

The at least one haptic foot pedal can also control at least one of camera angle, camera zoom, camera focus, irrigation, suction, robot brakes, electric coagulation, laser photocoagulation.

In a further aspect, the systems, etc., are directed to a local surgical cockpit comprising a local surgical console configured for transmitting surgical movements of an operator operating the local surgical console to a remote surgery site, and comprising at least one virtual console control knob presented virtually to the operator and configured to be manipulated by the operator to generate control signals for a corresponding remote device at a remote operation site.

The local surgical cockpit can be part of a system and the system further can comprise the corresponding remote device. The at least one virtual console control knob can be a binary switch configured to provide on/off signals to the corresponding remote device. The at least one virtual console control knob can be a gradual control knob configured to provide gradual control signals to the corresponding remote device. The virtual control knob can be operably connected to one of the three fingers of the haptic device. In some embodiments, the virtual control knob must be virtually gripped by two or more fingers of the haptic device before it may be rotated.

In still yet a further aspect, the systems, etc., are directed to at least two local surgical cockpits each comprising a surgical console configured for transmitting surgical movements of an operator operating the local surgical console to a distant remote surgery site located outside at least one building containing at least one of the surgical cockpits, wherein each cockpit can comprise a respective first and second set of at least two local robotic input arms configured to provide input to corresponding first and second remote sets of at least two corresponding remote robotic arms each configured to manipulate a remote surgical instrument at a single remote operation site, wherein the respective first and second set of local robotic input arms can be configured to be manipulated by respective first and second surgeons working in concert on the remote surgical site.

The local surgical cockpit system can be part of a further system and the further system further can comprise the first and second remote sets of at least two corresponding remote robotic arms. The distant remote surgery site can be located outside any building containing any of the local surgical cockpits. The system can be configured such that operators in different locales can operate simultaneously on a single surgical site; such that operators can relieve each other in a single surgery at a single surgical site; and/or to provide a teaching surgical cockpit and a student surgical cockpit providing haptic feedback to a student operator generated by a teaching operator. The haptic feedback to the student can comprise movements of a remote surgical instrument controlled by the teaching operator or tactile feedback from a surgical site being operated on by the teaching operator.

In still yet a further aspect, the systems, etc., are directed to a local surgical cockpit comprising a local surgical console configured for transmitting surgical movements of an operator operating the local surgical console to a remote surgery site, and comprising at least four local robotic input arms configured to provide input to a corresponding at least four remote robotic arms each configured to manipulate a remote surgical instrument at a remote operation site, wherein the at least four local robotic input arms can be configured to be manipulated by at least one surgeon operating the local surgical console.

The local surgical cockpit can be part of a system and the system further can comprise the four remote robotic arms operably connected to the four local robotic input arms such that the four remote robotic arms precisely respond to movements of the four local robotic input arms. The four remote robotic arms can be held in a sole arm-retention structure, which can be configured to hold the four remote robotic arms such that the arms cannot collide with each other. The cockpit can be part of a system comprising at least two local surgical cockpits each configured for an operator, and wherein the system can be configured such that each operator can simultaneously hold a single remote robotic arm, or such that the operators can switch control of a remote robotic arm between each other.

In another aspect, the systems, etc., are directed to a local surgical cockpit comprising a local surgical console configured for transmitting surgical movements of an operator operating the local surgical console to a remote surgery site, and comprising local 3-dimensional audio configured to obtain remote 3-dimensional audio input from a remote operation site and provide corresponding local 3-dimensional audio to an operator operating the console.

The local surgical cockpit can be part of a system and the system further can comprise remote 3-dimensional audio sensors operably connected to the local 3-dimensional audio such that the local 3-dimensional audio precisely transmit 3-dimensional audio signals from the remote 3-dimensional audio sensors. The 3-dimensional audio signals can be correlated with tactile feedback to provide correlated response to haptic input devices at the local surgical cockpit.

These and other aspects, features and embodiments are set forth within this application, including the following Detailed Description and attached drawings. Unless expressly stated otherwise, all embodiments, aspects, features, etc., can be mixed and matched, combined and permuted in any desired manner.

BRIEF DESCRIPTION OF THE DRAWINGS

FIG. 2 is a view of a fully relaxed body posture as observed in astronauts who are subjected to microgravity.

FIG. 3 is a second view of a fully relaxed body posture as observed in astronauts who are subjected to microgravity.

DETAILED DESCRIPTION

Figure 1:
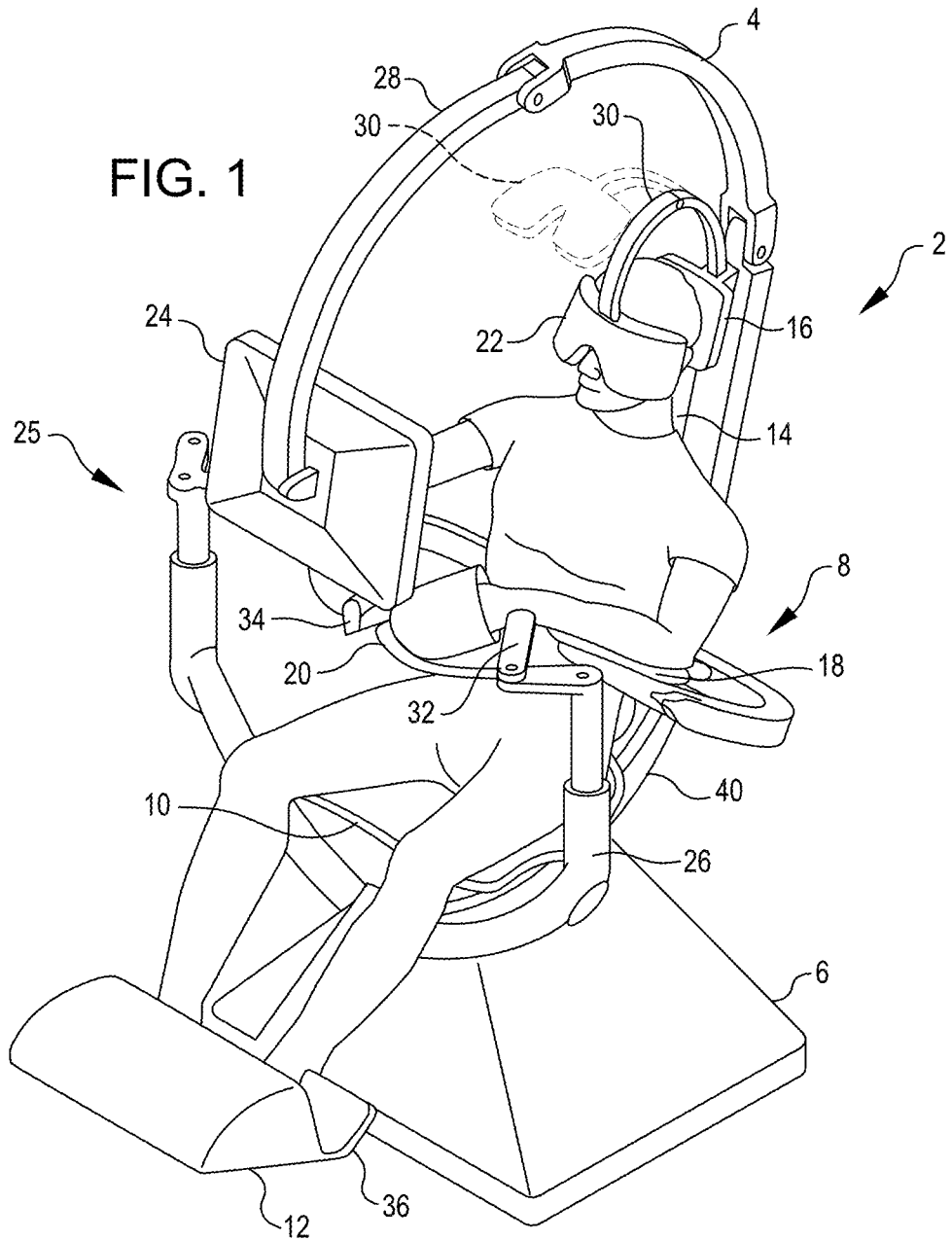
FIG. 1 depicts an isometric view of an exemplary cockpit and console according to various aspects and features discussed herein.

FIG. 1 depicts an exemplary cockpit and console according to various aspects and features discussed herein. Cockpit 2 comprises a surgical console 25 comprising screens, input devices and the like, and a structural frame 4 disposed on a base 6. The frame 4 provides physical support, directly or indirectly through other components, to the console components of the cockpit 2 such as robotic arms 20 and head mounted display 22 (HMD), and provides adjustable mounting capabilities for every desired element. In other embodiments, various console elements discussed herein can be disposed on other support structures instead of the frame 4, such as nearby walls, desks, tripod stands, etc.

The cockpits 2 herein can also comprise two or more different surgical consoles in one cockpit or two or more different surgical consoles in two or more different surgical cockpits that are operably connected to each other either locally or at the remote surgical site (or otherwise as desired). This allows, e.g., surgeons or other operators in completely different locales to operate or otherwise interact simultaneously on a single surgical site.

The seat 8 is an adjustable ergonomic seat that positions the body of the surgeon in a desired position such as an optimal, selectable posture to reduce fatigue or other discomfort. The seat 8 allows for positioning and orientation of its components (e.g., headrest 16, backrest 14, seat plate 10, footrest 12, armrests 18) in any possible configuration from sitting fully upright to a completely supine position and to accommodate different body types. Thus, positioning elements of the cockpit 2 are operably connected to the independently moveable headrest 16, backrest 14, seating plate 10, footrest 12 and armrest 18 to provide at least three axes of retainable positioning movement for each of those independently moveable elements relative to each other. For example, all such seating elements can be moveable relative to the frame, or one can be securely retained on the frame 2 and the other moveable seating elements can be moveable. The reference body posture can be the one adopted by the human body in microgravity.

Figure 5:
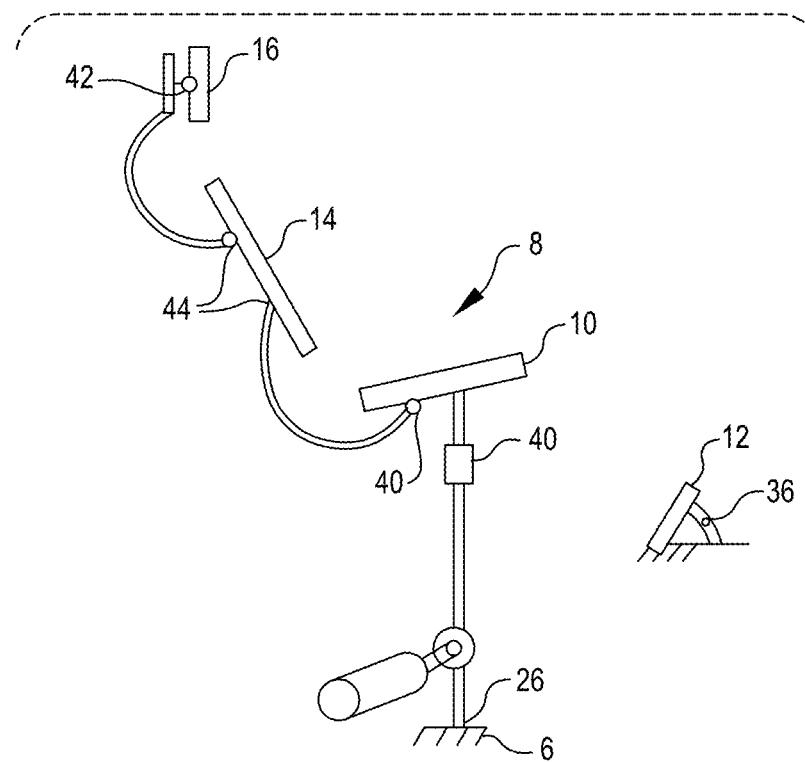
FIG. 5 depicts a side view of exemplary components of a seat as discussed herein.

As shown in FIG. 5 as well as FIG. 1 and other figures depicting the full cockpit, the joint 26 between the stationary base 6 and the frame 4 can be actuated to allow titling motion of the frame 4. The tilting motion accommodates the body position of the surgeon through different angles with respect to gravity. The tilting angle can range from a supine posture where the gravity vector is perpendicular to the spine, to a full upright posture where the gravity vector is parallel to the spine. During the tilting of the entire frame 4 as a whole, the relative position and orientation of the surgeon's body segments as well as the relative position and orientation with respect to the peripheral elements can be maintained. The backrest 14 of seat 8 can also comprise a variable lumbar support 96 that provides retainable positioning movement for support of the lower back.

As shown in this embodiment, the frame 4 is articulatable and provides the ability to removably attach and adjust peripheral devices such as monitors 24, HMDs 22 and forearmrests 18 and input devices 34 and for such peripheral devices to articulate in unison with respect to a stationary base 6 and/or seat 8. For example, when the seat position is modified, the location of the display and input device 34 move accordingly so that the relative position of the peripheral devices to the surgeon stays substantially the same. The adjustable elements of the seat allow body posture adjustments automatically or on demand. In the automatic mode, the chair positioning can be under the control of a high-level software module. The seat and other positioning elements can be moved electronically or mechanically via motors, manually, or otherwise as desired.

Articulated mechanical linkages and interfaces can be provided in the frame 4 for desired subsystems such as (1) two sets of articulated linkages 28, 30 for attaching the displays 50 such as an array of screens or monitors (one such monitor 24 is shown in FIG. 1 and FIG. 2 connected to articulated linkage 28) and the HMD 22, which is connected to HMD articulated linkage 30; (2) two interfaces 32 to support the arms and the input device 34; (3) a footrest support interface 36 to support the foot pedals 38 and the footrest 12; and, (4) a seat interface 40 to support the seat 8. All of these interfaces can be fully adjustable. Additional interfaces include headrest support interface 42 and backrest support interface 44. Friction based mechanical joints, or other suitable connectors, lock the cockpit 2 in the desired position. Interfaces that change their position frequently, such as interface 28 for the HMD 22, can be locked in place by electro-mechanical brakes.

A surgeon can be required to perform high dexterity manipulation during the course of surgery that may last for several hours. The chair can be designed such that it can be adjusted to emulate the same body posture as observed in astronauts who are subjected to microgravity (see FIGS. 2-4). In this body position the muscles reach their rest length and thus reduce potential fatigue. Moreover, the capability to adjust the body posture can be needed to avoid postural fixity, promote blood circulation, reduce joint pressure and muscle tension, and increase situational awareness In addition to the body posture, arm position affects the ability of the surgeon to control the input device 34 to the surgical robot. Arm manipulability can be a term that can define mathematically how joint angles (shoulder and elbow) are mapped into the hand position. It can be shown mathematically and proved experimentally that in order to maximize the manipulability, the elbow joint angle should be about 90°. Interestingly, this elbow joint angle can be also adopted by the human body in microgravity (see FIGS. 2-4—the elbow angle can be 92°+/−15°). Following this rationale, the arm of the surgeon can be positioned using adjustable armrests 18 with the same angles as indicated in FIGS. 2-4 to maximize the manipulability of the arm.

Figure 4:
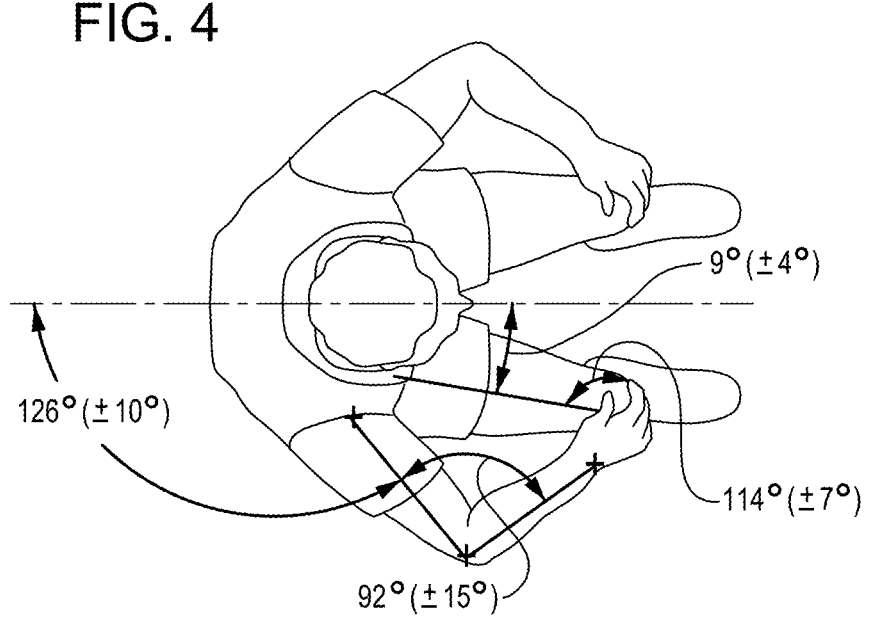
FIG. 4 is a third view of a fully relaxed body posture as observed in astronauts who are subjected to microgravity.

Footrest 12 supports the feet in a similar fashion to FIGS. 2-4 given the same rationale. This can enhance the ergonomic interactions between the surgeon's feet and hands with the controls and peripheral equipment. Further, the surgeon's foot can be fixed in space and ankle movements can be used to activate the pedals surrounding it. Functions such as controlling the cameras can be implemented by linking the ankle flexion/extension to the camera pitch movements and ankle rotation to the camera yaw movements. Haptics can be added to the pedals. For example, force feedback applied through the pedals can be correlated with camera position, or with irrigation or suction pressure.

Thus, the seat 8 can be adjusted to adapt to different bodies and changing body posture, automatically or on demand. This can avoid postural fixity, promote blood circulation, reduce joint pressure and muscle tension and increase situational awareness.

Figure 6:
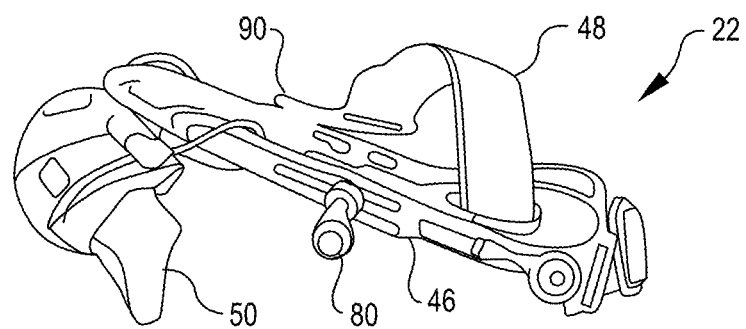
FIG. 6 depicts a head-borne HMD comprising a headset.

FIG. 1 shows a frame-mounted HMD 22; FIG. 6 depicts a head-borne HMD 22 comprising a headset 90. The embodiment in FIG. 6 comprises a head strap 46 and a vertical strap 48 and 3-D audio input device 80. The display 50 is disposed in front of the eyes of a user.

The display (HMD or otherwise such as a frame-borne monitor) can be divided into two components: (1) the hardware and (2) the information layout. From the hardware perspective, one or more, even several, 2-D and/or 3-D modalities can be used, for example two screens with projected mirrors, a Head Mounted Display with two separate streams of video displayed to each eye or a single 3-D screen, e.g., 120 Hz, with active and synchronized shutter glasses at 60 Hz (Nvidia 3-D Vision). For analyzing the graphical information available to the surgeon in the OR, an exemplary layout for a display 50 is summarized in Table 1 and depicted in FIG. 14:

| [Top Left] | [Main Display] | [Top Right] |
|---|---|---|
| 3-D remonstration of the target | 3-D display of Surgical Site | 2-D display of Mentoring Information |
| Augmented Information: | Augmented Information (on/off): | (e.g., textbook anatomy, model or video |
|   Preselected Margins to dissect |   Blood Pressure | clip of an expert performing the procedure, |
|   Masks of vital structures |   Temp | remote collaborator) |
| [Bottom Left] |   O2 SAT | [Bottom Right] |
| 2-D display of MRI CT scans |   CO2 | 2-D display of OR overview |
| (can be browsed) |   Intracranial pressure | |
| |   Preplanned trajectory | |
| |   Tool Type | |
| |   Suction On/Off | |
| | Bottom Task bar | |
| |   Recording capabilities | |
| |   Time | |
| |   Elapsed time | |

Figure 14:
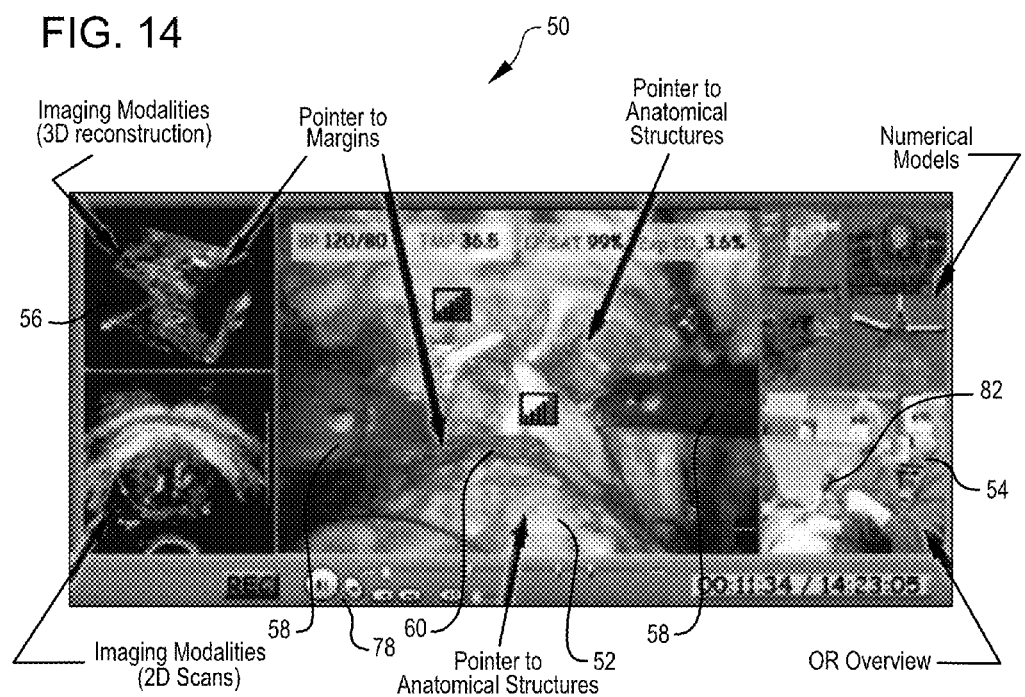
FIG. 14 depicts an exemplary conceptual layout of the visual information displayed by the cockpit to the surgeon

As can be seen in the Table and FIG. 14, the elements shown can include the remote surgical site 52, remote operating room 54, remote target 56 and remote surgical device 82 as well as other desired information. Such information can be presented in segments of a single screen or on multiple screens.

More specifically, FIG. 14 depicts an exemplary conceptual layout of the visual information displayed by the cockpit 2 to the surgeon. This layout translates the verbal specification and description listed in Table 1. High level software of cockpit 2 can manage the content of the display 50. The central view of the remote surgical site 52 point can be kept clear of overlays such as augmented reality by default if desired, with display of specific components under control of the surgeon. Information will flow to this display 50 from the endoscope/camera(s) targeting the remote surgical site 52 and remote target 56 within such site. In some embodiments, the display in FIG. 14 as well as haptic feedback and other information from the remote surgical site and/or operating room are transmitted to multiple local surgical cockpits. This allows, e.g., surgeons in completely different locales to operate simultaneously on a single surgical site with the same visual display, as depicted in FIG. 14, or with visual displays containing identical core information as well as additional custom information as desired by the surgeon. This also allows, e.g., surgeons in the same or different locales to relieve each other during a single surgery and for training surgeons with common tactile and visual feedback through the visual displays and haptic input devices, etc.

In this example the dissection plane can be shown as a deformable blue line; this direction line can be defined during the preoperative stage and can be tracked during surgery by the high level software. Force reflection signatures can be acquired as the position error between the input device 34 and the remote surgical instrument 58 by the high level software module from a low level software module, discussed further below. This information can be presented as colored dots attached to the surgical instruments (as overlays) to indicate safe (green) and unsafe (red) contacts for tissue resection. Patient vital signs can be optionally shown in the central view or docked in the display margins. This peripheral information can be acquired by the high level software module and present visually to the surgeon. Recording capabilities can be embedded into the main view and controlled by the high level software module allowing the surgeon to record the entire operation or individual segments (with chapter markers set by the surgeon if desired) to form a detailed medical record of the procedure as well as broadcast for teaching and remote conferencing. The additional monitors 24 present information acquired by imaging modalities along with an overview of the operating room or other information as desired. The nature of the information can be procedure specific.

Figure 7:
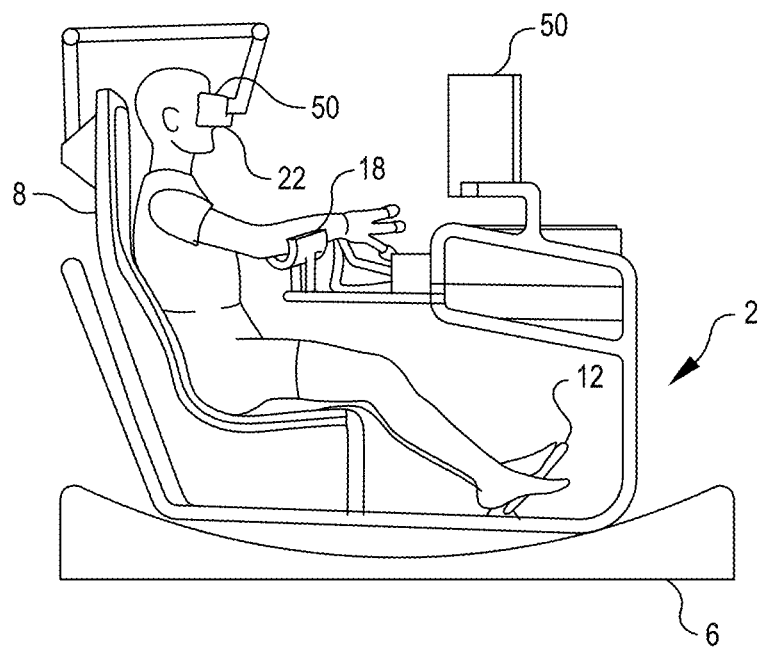
FIG. 7 depicts a side view of a further exemplary cockpit and console according to various aspects and features discussed herein.
Figure 8:
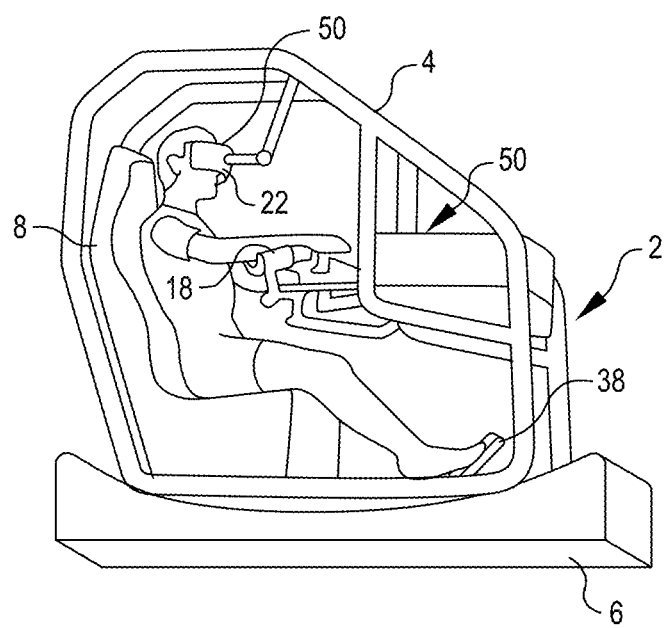
FIG. 8 depicts an isometric view of another exemplary cockpit and console according to various aspects and features discussed herein.
Figure 9:
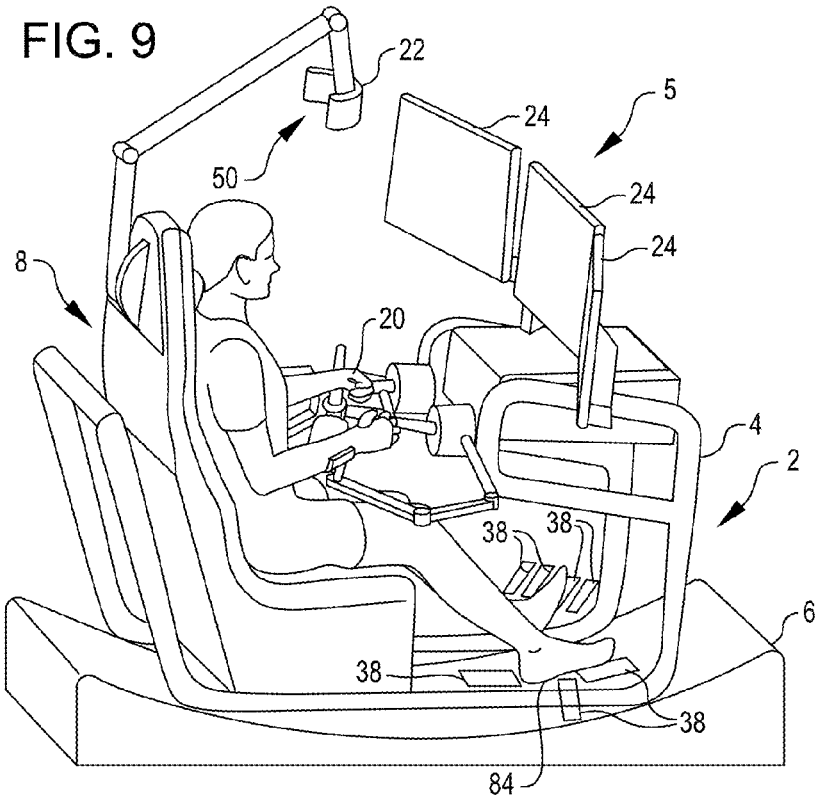
FIG. 9 depicts an isometric view of still a further exemplary cockpit and console according to various aspects and features discussed herein comprising an array of eight intuitive haptic foot pedals (four for each foot) that allows the surgeon to control multiple devices and to switch the control between them.

Returning to FIG. 1 and also referring to FIGS. 7-9, which depict various alternative cockpit embodiments and arrangements, the display 50 can be a modular display integrated into the surgical cockpit 2 with the following capabilities:

2-D and 3-D high definition visual displays (e.g., 1080 progressive lines) arranged in an array of 2-5 monitors 24. FIG. 9 shows an example with multiple monitors 24.

Head mounted display 22. The HMD can include two miniature screens located 2 cm away from each eye and fed by two separate streams of video signals to generate a stereoscopic image of the surgical scene. The HMD 22 can be mounted on an articulated boom 112 as in FIGS. 1 and 7-9, and can provide a redundant display to the flat panel array. In some embodiments, the HMD 22 displays only the remote surgical site 52, for situations where the surgeons wish to focus on the surgical site exclusively. The HMD can be mounted on any other suitable system such as a headset 90 as in FIG. 6 or other mechanisms such as several cables or parallel arms.

Synthesized display of multiple video sources fed from the endoscopic camera or surgical site camera, a camera of the OR, and along with applications presenting imaging information.

Desirable elements in the display design can include (1) reduced cognitive load for the surgeon, (2) support for surgical "flow", and (3) ultimately, increased patient safety. The displays, and other elements herein, can be used for both normal surgeries and for microsurgeries. Moreover, the microscope traditionally used for microsurgery may be replaced, such as with a 1-2 mm scope. This change provides a wider field of view.

In certain embodiments, the multiple (e.g., five) monitor layout and the HMD 22 present information in 3-D and provide support for various visualization, communication, and surgical performance functions, including (1) surgical instrument and the surgical scene—sensory information can be displayed for smart tools with embedded sensors; (2) two-handed haptic clinical information e.g. compression tension; (3) "augmented reality" blending graphical images with real-world views and real robot slaves e.g. go/no-go zones; (4) case archiving and videoconferencing for guiding and collaborative purposes. In order to provide a clean and informative interface while managing the cognitive load of the surgeon, every pieces of information presented on the display 50 can be called up or suppressed by the surgeon. This approach allows a custom display of information that can be dynamically changed during the surgical procedure.

Additional display 50 modalities include large field-of-view dome projection displays, which afford significantly larger display "real estate," and high-resolution autostereoscopic displays.

The augmented reality can also provide numerical models to indicate current tissue stresses propagating from instrument manipulations. The interface display, robot control commands, and/or audio can be recorded (with chapter markers set by the surgeon if desired) to form a detailed medical record of the procedure as well as broadcast for teaching and remote conferencing.

For example as shown in FIG. 9, the cockpit 2 can include at least two functional interfaces for the surgeon's hands (master robotic arm) and the feet (foot pedal array). As shown in FIG. 9 and other figures, the interfaces can include two robotic arms 20 and eight foot pedals 28 in two groups or sets of four. The surgeon controls all the specific functions of the surgical robot through these controls. The local controls also transmit force feedback to the surgeon as the remote surgical tools interact with the target tissue. Separate interfaces control peripheral devices such as positioning/zooming the camera, camera angle, camera focus, suctions/irrigation, robot brakes, and cautery including electric coagulation, laser photocoagulation, stapling, etc.

In some embodiments, as shown in FIG. 9, the first and second foot pedal sets can each contain four foot pedals 38. In one arrangement, as shown in front of the left foot of the seated figure in FIG. 9, the four pedals in can be arrayed in an arc in front of the user's foot. In another arrangement, as shown in front of the right foot of the seated figure in FIG. 9, the four pedals can each be in one of four quadrants of a circle, typically 90° apart. Opposed pairs can be assigned opposed functions at the remote surgical site, such as suction and irrigation. Each of the four pedals can also or alternatively be assigned complementary functions for a remote instrument(s) at the remote surgical site such as the viewing angles, focus, zoom, etc., of an endoscopic or operating room camera robot brakes, cautery such as electric coagulation or laser photocoagulation, etc.

The following discussion is directed to an exemplary individual input device 34, namely a robotic arm 20.

Turning to FIGS. 10-13, the master input device 34 is a multi degree of freedom (DOF) haptic device including two subsystems: (a) an articulated haptic arm 62 and (b) a three fingers haptic hand 64. Three capabilities that input device 34 typically includes to facilitate the fundamental control of surgical tools by the surgeon through the cockpit 2 comprise: (1) positioning and orientation of the tool tip in space requires 6 parameters—Cartesian position (x,y,z), and angular orientation (x y z θ, θ, θ); (2) scaling factors introduced such that the motion of the surgeon hands controlling the input device 34 can be scaled down (attenuate) or up (amplify) with respect to the robot; and, (3) indexing ("clutching"), which allows the surgeon to disengage the input device 34 from the robot to reposition his/her arms and engage again.

Two input devices 34 are typically fabricated and integrated into each cockpit 2—one for each hand of the surgeon. The arm 62 of the input device 34 can include six or seven DOF or more. The arm can be constructed as a cable actuated SCARA-based machine (SCARA-Selective Compliant Articulated Robot Arm), or otherwise as desired (as with all components of the systems discussed herein, unless specifically stated otherwise, the specific materials, manufacturing methods, etc., for the components can be selected to optimize particular features and characteristics. Thus, the components can be made of steel, carbon fiber, etc., so long as the composition is acceptable for the desired purpose).

A cable actuated system can be common practice in designing haptic devices. It allows for location of the actuators on a stationary base 6 to transfer torques to each one of the joints through a system of pulleys and cables. This configuration leads to a lightweight, low inertia, low friction, and back drivable haptic device that can reflect back to the user the forces generated when the surgical robot interacts with tissues. Back drivability can be an important characteristic of any force feedback haptic device. It generates a negligible effect of resistance as the operator moves the input device 34 in free space which can be the desired response as the surgical robot does not interact with any tissue.

The actuation and position sensors can be supported by a system of amplifiers, along with low level software modules incorporating servo feedback loops for tele-operation and force feedback control algorithms.

If actuators with high gear ratios are introduced to the system, the user feels the reflected inertia along with the friction in the gearbox—forces that mask the smaller effect of force feedback generated as a result of the interaction of the surgical robotic tool interacting with the tissue. The SCARA-based mechanism can be a classical robotic arm configuration which includes three consecutive axes with a rotation axis perpendicular to the ground or parallel to the gravitational vector. As a result, gravitational loads are not fully reflected into the actuated joint and most of the load can be supported by the structure elements of the haptic device and not by the actuator associated with the joint—a situation that leads to use of smaller actuators for the joint.

Force feedback can be eliminated from the operational mode of the system if so desired. In such a situation, actuators are still typically incorporated into the tactile input device 34. Their secondary can be to preserve the registration between the input device 34 and the remote surgical tool by locking the orientation of the tip of the input device 34 (arm) once indexing is taking place. Indexing should typically only allowed for repositioning the end effector of the input device 34 in the Cartesian space (x,y,z) through translation or repositioning. The orientation of the input device 34 during the indexing process must typically be preserved. Reorientation is not typically allowed during the indexing process in order to preserve the registration between the input device 34 of the cockpit 2 and the surgical tool attached to the surgical robot.

Force feedback capabilities can be achieved by a cable driven master mechanism with a set of actuators (e.g., brushed DC motors) and position sensors (encoders and potentiometers) attached to its base. Brushless DC motors have a minor advantage compared with brushed motors as far as torque to weight ratio. However the high numbers of electrical wires for motor commutation may cancel out their minor advantage.

For example, the actuators can be selected to generate the following peak forces and torques: (1) translational forces 67 N, grasping force 42 N, torques 2.4 Nm. The actuation and position sensors can be supported by a system of amplifiers, along with newly developed low-level software modules incorporating servo feedback loops for teleoperation and force feedback control algorithms.

In another example, the input device 34 comprises: (1) the direct kinematics of the haptic arm defined by mapping the joint angle to the end effector (hand interface), (2) The Jacobian matrix can be derived by mapping the joint angular velocity to the end effector velocities, (3) the manipulability as a performance measure can be defined, (4) a cost function can be defined taking into account the manipulability measure and the link length of the mechanism. Using a brute force numerical solution, for example, the cost function can be calculated across an entire workspace of different combinations of link lengths, for example ones that have maximal dynamic manipulability with the minimal link lengths within a workspace of 10×10×10 cm.

Figure 10:
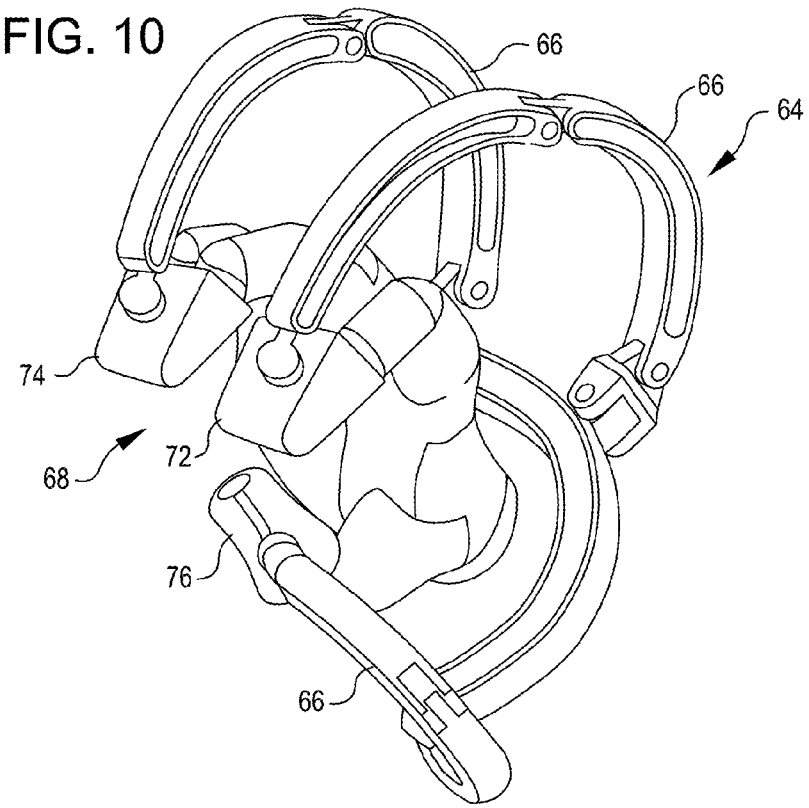
FIG. 10 depicts an isometric view of a three fingers haptic hand wherein the middle and index fingers are lumped into a first port, the ring and the fifth finger are lumped into a second port and the thumb is in third port.
Figure 12:
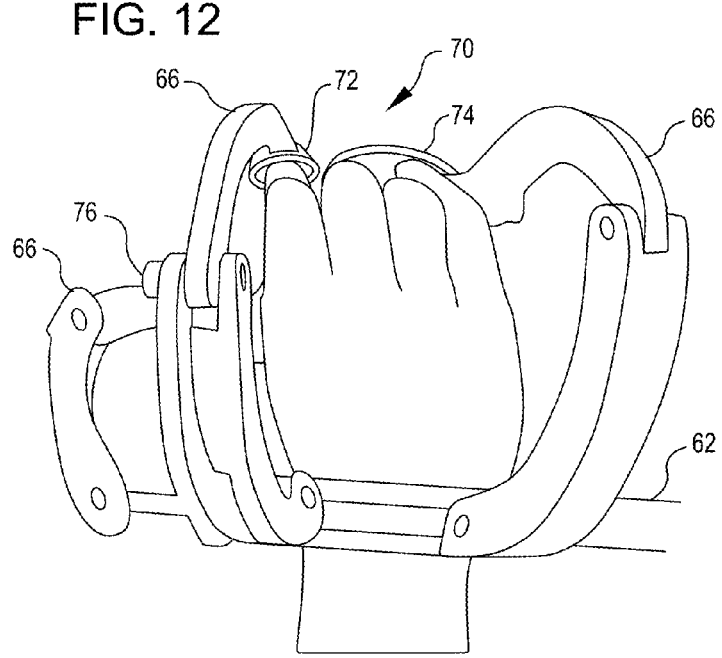
FIG. 12 depicts a top view of a three fingers haptic hand wherein the index finger is lumped into a first port, and the middle, ring and fifth finger are lumped into a second port, and the thumb is in third port.
Figure 13:
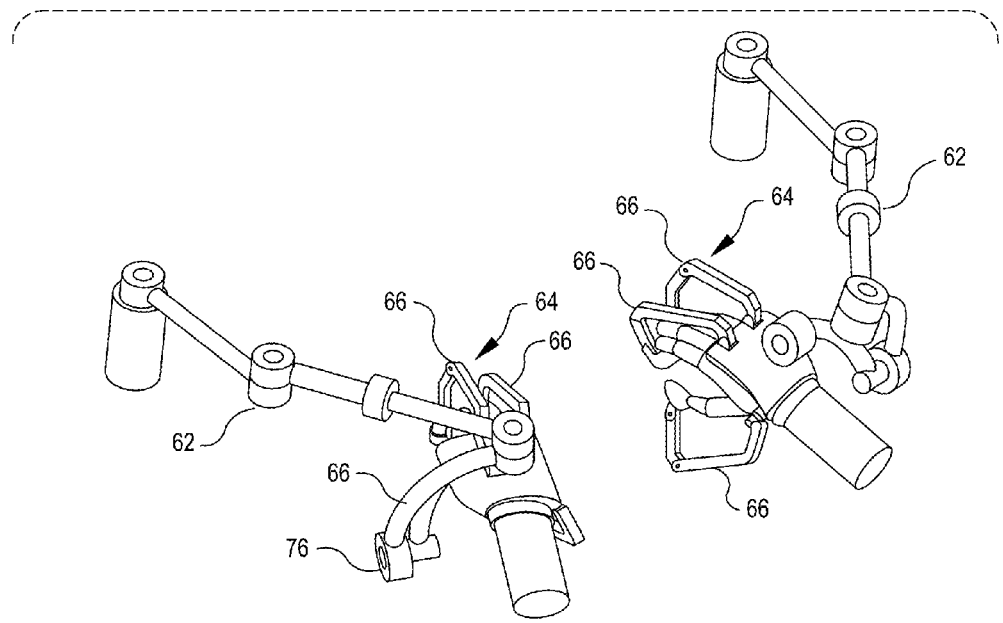
FIG. 13 depicts an isometric view of an articulated haptic arm coupled to a three fingers haptic hand.

The surgeon's hands interact with the master devices through a three-finger mechanical interface such as the three fingers haptic hand 64. In FIG. 10, the middle and index fingers are lumped into the first port 72, the ring and the fifth finger are lumped into the second port 74 and the thumb is in third port 76. In FIG. 12, the index finger is put into the first port 72, the middle, ring and the fifth finger are lumped into the second port 74 and the thumb is in third port 76.

Figure 11:
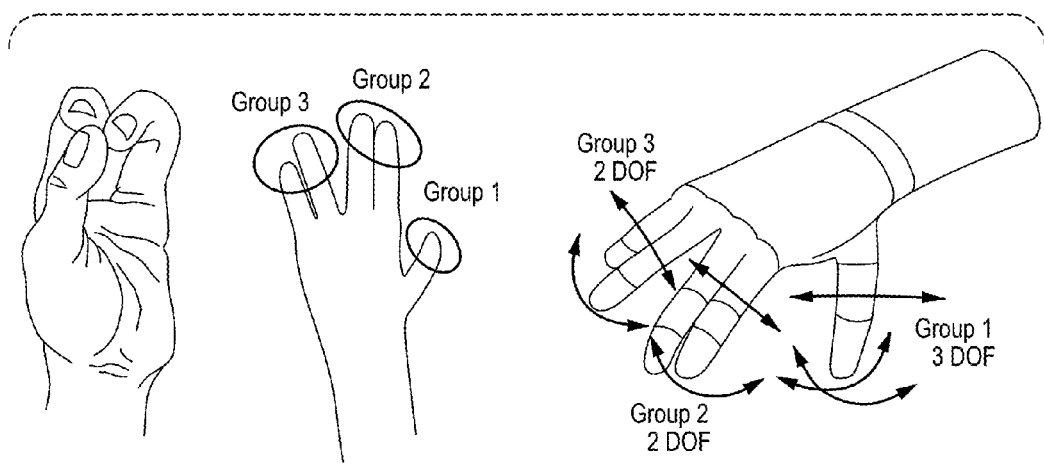
FIG. 11 shows some of the degrees of freedom obtainable with a three-fingered hand.

The 3 fingers interface mediates the significant gap between the 5 fingers (5 fingers×4 DOF per finger=20 DOF) of the human hand and 2 fingers systems having only 1 DOF. FIG. 11 shows some of the degrees of freedom obtainable with a three-fingered hand. Thus, the three fingers interface allows a wide spectrum of control capabilities by the surgeon's hand over a remote surgical instrument or other remote device.

The haptic hands herein can switch between various user-finger configurations to maximize dexterity as desired. Each of the tactile devices such as the robotic arm 62 and three fingers haptic hand 64 can comprise 12 DOF or more.

Information perceived through the human sense of touch (haptics) can be classified into two categories, cutaneous and kinesthetic. Cutaneous information can be provided via the mechano-receptive nerve endings in the glabrous skin of the human hand. It can be primarily a means of relaying information regarding smallscale details in the form of skin stretch, compression and vibration. Kinesthetic sensing encompasses larger scale details, such as basic object shape and mechanical properties, for example, compliance. This can be achieved via feedback from the muscular and skeletal system.

If desired, not all DOF need have tactile (haptic) feedback. For example, only 3 out of the 6 DOF that can be sensed for the three fingers mechanism may include force feedback. Thus, in some embodiments, there will be a reduction from 12 potential actuated DOF in the arm-hand combination to only 9 fully actuated DOF with force feedback at the hand (fingers). For example, the remaining 3 non-actuated DOF will can be position information that can be provided by the low frequency motion of the hand and the arm, cutaneous information can be provided to the surgeon regarding tissue texture via high frequency actuators incorporated into the finger pad interface of the 3 fingers hand. Low frequency indicates forces provided in the range of 0-100 Hz; high frequency indicates forces provided in the range of 100 Hz and higher.

The following functions were identified for the third finger: microscope control, suction, irrigation, drilling, clutching. In order to provide full control of these functions, two types of buttons can be implemented: (1) binary button (On/Off); (b) gradual knob (Volume/Magnitude).

| Master Device Joint | DOF | DOF with Force Feedback |
|---|---|---|
| Shoulder | 2 | 2 |
| Elbow | 1 | 1 |
| Wrist | 3 | 3 |
| 3 Fingers | 6 | 3 |
| Total | 12 | 9 |

In certain embodiments, each finger has force feedback on 2 out of the 3 DOF allowing flexion/extension movements and feedback. The fingers' adduction/abduction movements can be supported by a passive DOF with no force feedback.

The three-finger design is particularly useful for use with (1) virtual knobs and switches 78 (such as shown in FIG. 14). For example, to control retractors, electrocoagulators, or view of the scene and (2) anticipating new tool designs in the future, it allows the surgeon to regain the level of dexterity and manipulability of the human hand used in open surgery but lost in current robotic systems. The virtual control knob can be operably connected to one or more of the three fingers of the haptic input device(s). The virtual control knob can also be configured so that it must be virtually gripped by two or more fingers of the haptic device before it may be rotated or otherwise manipulated.

FIG. 9 depicts a cockpit 2 comprising an array of 8 intuitive haptic foot pedals (4 for each foot) that allows the surgeon to control multiple devices and to switch the control between them. Two desirable pedal configurations: (1) serial arrangement (similar to a car) and (2) spatial arrangement in which 4 pedals surround each foot such that by flexing/extending the ankle and rotating the feet left/right all 4 pedals are accessible. The serial arrangement can be limited to 3 pedals for each foot. Increasing the number of pedals beyond three makes it difficult for the surgeon to locate the pedals while being immersed visually in the surgical site. The spatial arrangement of 4 pedals sounding the feet from 4 different orthogonal directions provides an easier registration between the feet and the pedals and a richer medium as an input device 34.

The feet tactile interface can include a passive gimbal mechanism 84 to support the heel of the foot. The gimbal mechanism 84 allows the surgeon to move freely in any direction while avoiding gamble lock (the rotation in any direction will never exceed 90°). The four pedals can be arranged around the distal end of the feet in four orthogonal planes. Flexing the ankle joint will press the top pedal while extending the joint will press the bottom pedal. Moving the distal part of the foot left and right will press the left and right pedals.

A dead zone can be implemented in the design preventing a situation in which the feet activate two opposing functions simultaneously (e.g., suction and irrigation). Each pedal can be controlled by a single DC servo motor. Through the software, the force displacement characteristics can be defined. Displacement characteristics of each pedal provide the opportunity to change the function of this interface and assign functions to each pedal based on a specific operation (similar to the third finger of the hand interface). Moreover, the software can allow the surgeon to change the nature of the pedal from an on/off switch to a gradual control switch.

The distribution of functions between the hand's third finger and the foot can be assigned as desired. Functions such as controlling the cameras can be implemented by linking the ankle flexion/extension to the camera pitch movements and ankle rotation to the camera yaw movements. Haptics can be added to the pedals. For example, force feedback applied through the pedals can be correlated with irrigation or suction pressure.

As noted previously, the cockpits 2 herein can also comprise two or more different surgical consoles in one cockpit or two or more different surgical consoles in two or more different surgical cockpits that are operably connected to each other either locally or at the remote surgical site (or otherwise as desired). This allows, e.g., surgeons in completely different locales to operate simultaneously on a single surgical site. This also allows, e.g., surgeons in the same or different locales to relieve each other in a single surgery at a single surgical site. This still further allows, e.g., exceptional training of surgeons one by another, including providing tactile feedback to a student surgeon, for example from the movements of the surgical instruments controlled by the teaching surgeon or to the student surgeon from a surgical site being operated on by the teaching surgeon.

Figure 15:
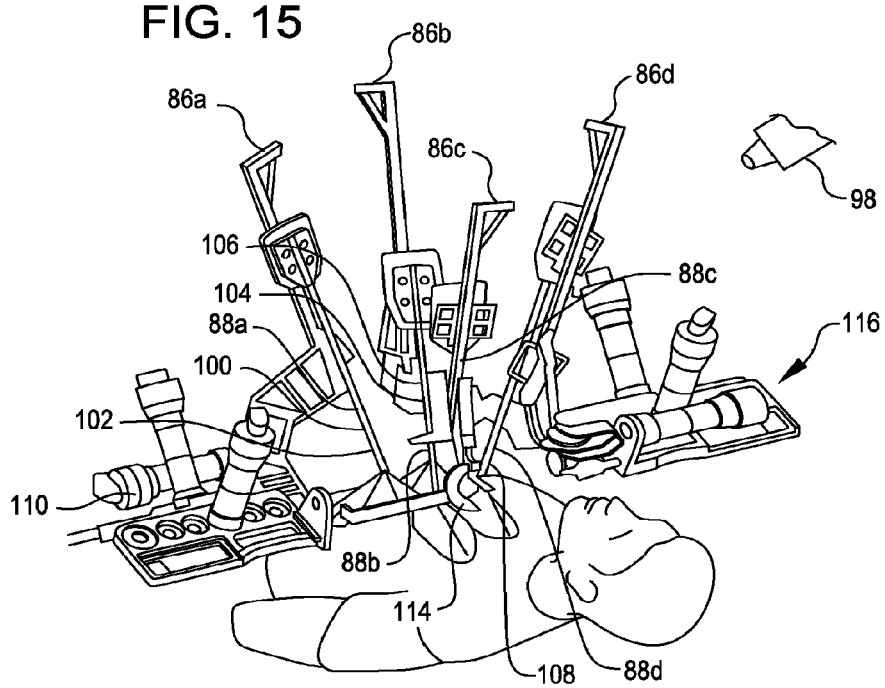
FIG. 15 depicts an isometric view of four robotics arms that can be teleoperated by one or two surgeons in multiple modes of operation

FIG. 15 depicts an isometric view of a system comprising four remote robotics arms 86a-86d holding remote surgical instruments 88a-88d in a remote operating room, which arms 86 can be teleoperated by one or two (or more) surgeons in multiple modes of operation, such as (1) solo by a single surgeon from a local or a remote location (2) by two surgeons in which one or both are located locally with the robot or in one or two remote sites.

The four robotic arms can contain a variety of peripheral devices and/or functions, such as an endoscope 100 comprising an endoscopic camera 102 in remote surgical instrument 88a coupled with positioning and/or zooming the camera, camera angle, camera focus. Similarly, remote surgical instrument 88b can contain a suction device 104 and irrigation device 106, and remote surgical instrument 88d comprises a cautery device 108 for, for example, electric coagulation or laser photocoagulation. The robotic arms can also be under the control of robot brakes 110 and can provide a staple applier 114.

The four arms 86 system duplicates two surgeons collaborating and simultaneously interacting with the remote surgical site. The new system provides a new opportunity to explore collaborative surgery which to some extent was not possible before due to the limited number of available remote surgical arms 86. Moreover, the control over one or two of the arms can be assigned to an artificial agent (software) and to facilitate new methods of automation. In certain embodiments, any robotic arm can be assigned at any point by the primary surgeon to the other surgeon(s) or the artificial agent regardless of its location (local or remote).

In certain embodiments, the four remote robotic arms are held in a sole arm-retention structure 116. The sole arm-retention structure can be configured to hold the four remote robotic arms such that the arms cannot collide with each other.

The cockpit can be part of a system comprising at least two local surgical cockpits each configured for an operator, and the system can be configured such that each operator can simultaneously hold a single remote robotic arm, and/or so that that the operators can switch control of a remote robotic arm between each other.

FIG. 15 also depicts an external, remote operating room camera 98. The functions of this camera such as position, zooming, angle, focus, etc., and other remote operating room devices and peripherals can also be controlled by the surgeon or other operator in the surgical cockpit 2.

FIG. 6 depicts an exemplary headset 90 comprising a 3-D auditory input device 80. The Auditory Interface can be any suitable 3-D auditory system such as a system comprising two sonic beam focused speakers. 3-D auditory technologies include Hypersonic Sound (HSS) by American Technology Corp and Audio Spotlight by Holosonics. These technologies allow a focal beam of sound to be transmitted into a specific point in space (surgeon's ears) and avoid sound "pollution" in the operating room (OR). Both can still provide desired sound input from the operating room.

3-D auditory input devices 80 permit local surgical areas/cockpits to become consistent virtual listening areas without the pervasive omnidirectionality of conventional loudspeakers. The high-precision targeting of directional beam of sound significantly minimizes the levels of noise pollution in the local operating rooms while still allowing the surgeon to respond to other sources of auditory inputs from the remote operating room.

The 3-D auditory input devices 80 can be used, for example, to convey the following information via either natural or synthetic sound cues: (1) collisions between the surgical tools, (2) contact between the tool tip and some types of tissue, (3) stress levels applied to the tissue, (4) vital signs and emergency limits, (5) local pulse and vascular blood flow to denote vessels that may need to be preserved or ligated.

There are several types of 3D audio effects, such as (1) widening the stereo image by modifying phase information; (2) placing sounds outside the stereo basis and (3) complete 3D simulation. Sound can be complementary to haptics because little kinesthetic information extends into the audio frequency range. Audio may play an important role in perceiving the important information generated by the surgical site or the OR by the surgeon located in a remote site.

Figure 16:
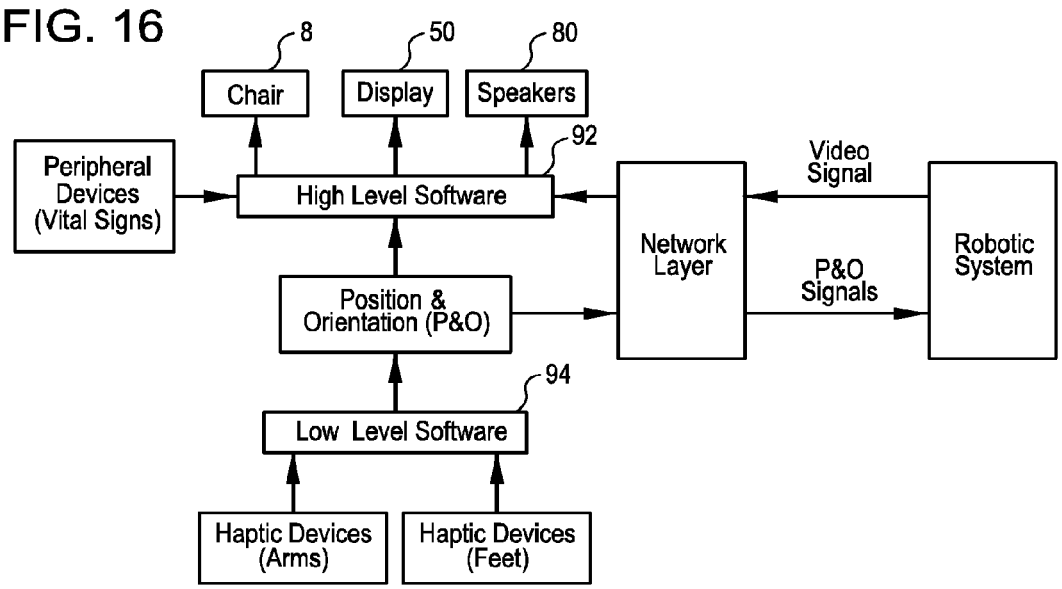
FIG. 16 is a block diagram depicting certain aspects of an exemplary software architecture that can be used with the local surgical cockpits and remote surgical procedures herein.

FIG. 16 is a block diagram depicting certain aspects of an exemplary software architecture that can be used with the local surgical cockpits 2 and remote surgical procedures herein. In this example, the software architecture includes two layers: high level software 92 and low level software 94. The software comprises multiple interfaces to peripheral hardware and software components such as seat 8, display 50 and 3-D audio input devices 80. The software can also be used for the surgical cockpit 2 to communicate with any desired surgical module (surgical robot) that shares a proper communication channel such as a common and universally accepted Transmission Control Protocol/Internet Protocol (TCP/IP). Thus, the surgical cockpit can not only be used with nearby remote surgical sites but also with distant remote surgery sites located outside at least one, and possibly any, building containing at least one of the surgical cockpit(s).

The high level software 92 can comprise a software layer that smoothly interfaces the teleoperation capability with image-guided software modules residing either at the remote or local surgeon site, and a software module that facilitates collaborative communication among multiple surgical consoles. The high-level software module 92 can merge the information provided by the hand, foot, and peripheral input device 34. Image data and vital signs are presented continuously and/or through computer generated audio cues. The high level module can be divided into processes, and if desired each process can be dedicated to one of the peripheral elements depicted in FIG. 8.

The low level software 94 can comprise a robust software layer that leverages control techniques to support haptic feedback via Internet connections at local, national, and global scales. The low-level software module can be responsible for the interpretation of the low-level input signals acquired from the hand and feet interfaces. Signals are translated to and from the surgical robot over a network using TCP/IP.

Network communications can update the software modules, for example the high level module that manages visual and audio display.

The low level software can be primarily a real-time segment of the software running on a RT Linux operating system. The high level module can be non real-time software.

If desired, the interaction between the high level and low level modules can be primarily unidirectional, in which position and orientation of the surgical tool location can be sent from the low level to the high level, with the only exception in which information can be sent back to the low level module being when a tool reaches a position that exceeds a predefined safe zone.

As may be seen from the foregoing, the present invention provides an improved surgical device that permits surgical instruments to reach remote portions of the body with reduced trauma. The device sheath may be steered to a surgical site around sensitive or critical tissue. The surgical tool components may be removed for replacement or cleaning without the device having to be straightened or removed from the body. Further, the tool deflection assemblies and methodology renders precise control of the surgical tool components in all required degrees and directions of movement. The present invention is thus well suited for use in many different applications, including robotic surgical systems.

From the foregoing, it will be appreciated that, although specific embodiments have been discussed herein for purposes of illustration, various modifications may be made without deviating from the spirit and scope of the discussion herein. Accordingly, the systems and methods, etc., include such modifications as well as all permutations and combinations of the subject matter set forth herein and are not limited except as by the appended claims or other claim having adequate support in the discussion and figures herein.

What is claimed is:

1. A system for performing remote surgery, the system comprising:
   a plurality of local surgical cockpits configured such that
      a plurality of operators in different locales can operate simultaneously on a single remote surgical site, wherein each local surgical cockpit of the plurality of local surgical cockpits comprises a local surgical console configured for transmitting surgical movements of an operator operating the local surgical console to the remote surgery site, each local surgical console comprising a plurality of local input surgical fingers configured to provide input to a remote surgical instrument at the remote surgery site, wherein the plurality of local input surgical fingers of each local surgical console comprises a cable actuated mechanism configured to provide high frequency haptic feedback to the corresponding operator based on acceleration of the corresponding remote surgical instrument.

2. The system of claim 1, wherein the plurality of local input surgical fingers is configured to provide input to a remote robotic arm coupled to the corresponding remote surgical instrument.

3. The system of claim 1, wherein the plurality of local surgical cockpits are configured such that the plurality of operators can switch control of a single remote surgical instrument between each other.

4. The system of claim 1, wherein the plurality of local surgical cockpits are configured such that each operator of the plurality of operators controls a different remote surgical instrument.

5. The system of claim 1, wherein the plurality of local surgical cockpits comprises a teaching surgical cockpit and a student surgical cockpit providing haptic feedback to a student operator generated by a teaching operator.

6. The system of claim 5, wherein the haptic feedback to the student comprises movements of a remote surgical instrument controlled by the teaching operator.

7. The system of claim 5, wherein the haptic feedback to the student comprises tactile feedback from a surgical site being operated on by the teaching operator.

8. A system for performing remote surgery, the system comprising:
a plurality of local surgical cockpits configured such that a plurality of operators in different locales can operate simultaneously on a single remote surgical site, wherein each local surgical cockpit of the plurality of local surgical cockpits comprises a local surgical console configured for transmitting surgical movements of an operator operating the local surgical console to the remote surgery site, each local surgical console comprising at least three input fingers configured to provide input to a corresponding remote surgical device at the remote surgery site,
wherein the at least three input fingers of each local surgical console comprise a cable actuated mechanism configured to provide high frequency haptic feedback to the corresponding operator, and wherein the at least three input fingers of each local surgical console are configured to be manipulated by a single hand of the corresponding operator operating the local surgical console.

9. The system of claim 8, further comprising the remote surgical device associated with at least one local surgical console, wherein the remote surgical device is operably connected to the at least three input fingers of the at least one local surgical console such that the remote surgical device is configured to precisely respond to movements of the at least three input fingers.

10. The system of claim 8, wherein the at least three input fingers of each local surgical console comprise a first port shaped to receive the operator's thumb, a second port shaped to receive the operator's index and middle fingers, and a third port shaped to receive the operator's ring and little fingers.

11. The system of claim 8, wherein the at least three input fingers of each local surgical console comprise a first port shaped to receive the operator's thumb, a second port shaped to receive the operator's index finger, and a third port shaped to receive the operator's middle, ring, and little fingers.

12. The system of claim 8, wherein the at least three input fingers of each local surgical console are configured to provide haptic feedback to the corresponding operator based on interaction of the corresponding remote surgical device with tissue.

13. The system of claim 8, wherein the at least three input fingers of each local surgical console are operably connected so that two input fingers control the corresponding remote surgical device and the remaining third input finger controls a corresponding second device.

14. The system of claim 13, wherein the second device is one or more of an electrocautery device, a laser photocoagulator, or a staple applier.

15. The system of claim 13, wherein the second device is a camera system and the remaining third input finger controls one or more of focus, zoom, rotation, or field-of-view of the camera system.

16. A system for performing remote surgery, the system comprising:
a plurality of local surgical cockpits configured such that a plurality of operators in different locales can operate simultaneously on a single remote surgical site, wherein each local surgical cockpit of the plurality of local surgical cockpits comprises a local surgical console configured for transmitting surgical movements of an operator operating the local surgical console to the remote surgery site, each local surgical console comprising:
a plurality of local input surgical fingers comprising a cable actuated mechanism configured to provide high frequency haptic feedback to the corresponding operator;
a display; and
at least one virtual console control knob presented virtually to the corresponding operator on the display and configured to be manipulated by the corresponding operator to generate control signals for a corresponding remote device at the remote surgery site,
wherein the at least one virtual control knob is operably connected to at least one of the plurality of local input surgical fingers.

17. The system of claim 16, wherein the virtual control knob of each local surgical console is configured to be rotated in response to a gripping input from at least two of the corresponding plurality of local input surgical fingers.

18. The system of claim 1, wherein each local surgical console further comprises a stationary base and the plurality of local input surgical fingers is mechanically coupled to the stationary base via an articulated mechanical linkage.

19. The system of claim 8, wherein each local surgical console further comprises a stationary base and the at least three input surgical fingers are mechanically coupled to the stationary base via an articulated mechanical linkage.

20. The system of claim 16, wherein each local surgical console further comprises a stationary base and the plurality of local input surgical fingers are mechanically coupled to the stationary base via an articulated mechanical linkage.

* * * * *